(12) United States Patent
Otsuka et al.

(10) Patent No.: US 9,274,555 B2
(45) Date of Patent: Mar. 1, 2016

(54) WEARABLE ELECTRONIC DEVICE

(71) Applicant: Panasonic Intellectual Property Management Co., Ltd., Osaka (JP)

(72) Inventors: Yu Otsuka, Osaka (JP); Yukinari Inoue, Shizuoka (JP); Hiraku Hamanaka, Miyagi (JP); Mitsuaki Terui, Miyagi (JP); Hiroshi Fujita, Osaka (JP); Goro Hisatake, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 14/578,993

(22) Filed: Dec. 22, 2014

(65) Prior Publication Data

US 2015/0185766 A1 Jul. 2, 2015

(30) Foreign Application Priority Data

Dec. 27, 2013 (JP) ................. 2013-273471

(51) Int. Cl.
*G06F 1/16* (2006.01)
*A61B 5/024* (2006.01)
*A61B 5/00* (2006.01)

(52) U.S. Cl.
CPC ............ *G06F 1/163* (2013.01); *A61B 5/02422* (2013.01); *A61B 5/681* (2013.01);
(Continued)

(58) Field of Classification Search
CPC .. A61B 5/6831; A61B 5/6824; A61B 5/0242; A61B 5/0053; A61B 5/681; A61B 5/02422; G06F 1/1698; G06F 1/1635; G06F 1/163
USPC ............... 361/679.01–679.09, 679.1–679.19, 361/679.21–679.29, 679.31–679.45, 361/679.55–679.6; 224/152; 345/156, 157, 345/168, 169; 600/300, 301, 595; 24/71 J, 24/265 WS
See application file for complete search history.

(56) References Cited

U.S. PATENT DOCUMENTS

| | | | | |
|---|---|---|---|---|
| 6,035,035 A | * | 3/2000 | Firooz | .................... H04B 1/385 379/433.1 |
| D661,275 S | * | 6/2012 | Roka | .............................. D10/31 |

(Continued)

FOREIGN PATENT DOCUMENTS

| | | |
|---|---|---|
| CH | 591222 | 9/1977 |
| DE | 2837056 | 3/1980 |

(Continued)

OTHER PUBLICATIONS

The Extended European Search Report dated Apr. 30, 2015 for the related European Patent Application No. 14198584.6.

*Primary Examiner* — Hoa C Nguyen
*Assistant Examiner* — Sagar Shrestha
(74) *Attorney, Agent, or Firm* — McDermott Will & Emery LLP

(57) ABSTRACT

A wearable electronic device according to the present disclosure includes a first belt, front surface of the first belt being provided with a displaying unit having a curved display face; a second belt; a hinge that connects a first end of the first belt to a first end of the second belt. A shape of a space formed by the first and second belts is an elliptical shape when the device worn around a subject is viewed from a side. The hinge has higher flexibility than the first and second belts. The device has a first engagement unit provided at a second end and a rear surface of the first belt, and in a region where the elliptical shape has smaller curvature than other regions. The device has a second engagement unit provided at an outer side of the second belt and engaging with the first engagement unit.

14 Claims, 12 Drawing Sheets

(52) U.S. Cl.
CPC ........... *G06F 1/1635* (2013.01); *G06F 1/1698* (2013.01); *A61B 5/0053* (2013.01); *A61B 5/6824* (2013.01); *A61B 5/6831* (2013.01)

(56) References Cited

U.S. PATENT DOCUMENTS

| | | | |
|---|---|---|---|
| D725,068 S * | 3/2015 | Cho | D14/138 R |
| 2004/0209657 A1* | 10/2004 | Ghassabian | H04B 1/385 455/575.1 |
| 2005/0174302 A1 | 8/2005 | Ishii | |
| 2006/0202618 A1* | 9/2006 | Ishii | G04B 37/12 313/513 |
| 2008/0084657 A1 | 4/2008 | Baba et al. | |
| 2012/0253485 A1* | 10/2012 | Weast | G06F 19/3481 700/91 |
| 2013/0335929 A1 | 12/2013 | Cavallaro | |
| 2014/0135592 A1* | 5/2014 | Ohnemus | A61B 5/7275 600/301 |
| 2015/0049591 A1* | 2/2015 | Adams | G04G 21/08 368/13 |
| 2015/0185762 A1* | 7/2015 | Magi | G06F 1/163 361/679.03 |

FOREIGN PATENT DOCUMENTS

| | | |
|---|---|---|
| GB | 852466 | 10/1960 |
| JP | 8-150223 | 6/1996 |
| JP | 10-051527 | 2/1998 |
| JP | 2001-512581 | 8/2001 |
| JP | 2005-117224 | 4/2005 |
| JP | 2007-078670 | 3/2007 |
| JP | 2008-096543 | 4/2008 |
| JP | 2012-190321 | 10/2012 |
| WO | 98/36309 | 8/1998 |

* cited by examiner

FIG. 13A
FIG. 13B
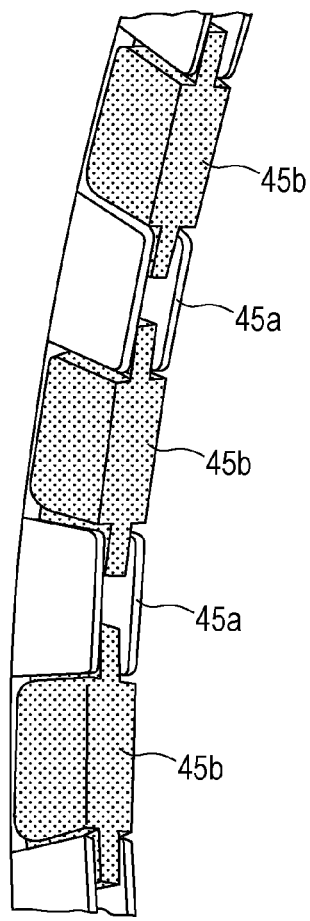
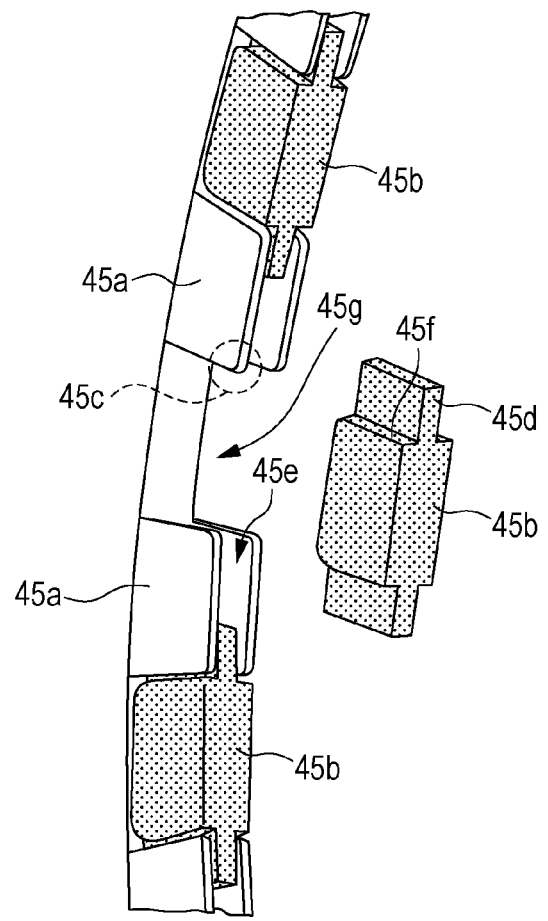

WEARABLE ELECTRONIC DEVICE

BACKGROUND

1. Technical Field

The present disclosure relates to electronic devices. In particular, the present disclosure relates to a wearable electronic device.

2. Description of the Related Art

In recent years, multifunction portable terminals that are made based on the functions of computers, that is, so-called smartphones, are quickly becoming popular. Moreover, arm-wearable portable terminals, that is, so-called smartwatches, as wearable multifunction portable terminals are being developed.

SUMMARY

With regard to a wearable portable terminal, it is necessary to arrange components in view of fittability of the portable terminal. Generally, fittability improves with increasing number of flexible portions in the portable terminal. However, a portable terminal tends to decrease in reliability and break more easily, with increasing number of flexible portions.

One non-limiting and exemplary embodiment provides a highly-reliable, readily-wearable electronic device by ensuring a non-flexible portion therein.

Additional benefits and advantages of the disclosed embodiments will be apparent from the specification and figures. The benefits and/or advantages may be individually provided by the various embodiments and features of the specification and figures, and need not all be provided in order to obtain one or more of the same.

A wearable electronic device according to an aspect of the present disclosure includes a first belt, front surface of the first belt being provided with a display having a curved display face; a second belt; a hinge that connects a first end of the first belt to a first end of the second belt. A shape of a space formed by the first and second belts is capable of an elliptical shape when the electronic device worn around a subject is viewed from a side of the wearable electric device. The hinge has higher flexibility than the first and second belts. The wearable electronic device has a first engagement unit that is provided at a second end and a rear surface of the first belt, the second end of the first belt being opposite the first end of the first belt. The first engagement unit is provided in a region of the rear surface of the first belt, in the region, the elliptical shape having smaller curvature than other regions of the elliptical shape. The wearable electronic device has a second engagement unit that is provided at an outer side of the second belt and that engages with the first engagement unit.

According to the present disclosure, a highly-reliable, readily-wearable electronic device is achieved by ensuring a non-flexible portion therein.

These general and specific aspects may be implemented using a system, a method, and a computer program, and any combination of systems, methods, and computer programs.

BRIEF DESCRIPTION OF THE DRAWINGS

FIG. 13A illustrates the configuration of the second embodiment of the sidewall of the battery cover;

FIG. 13B illustrates the configuration of the second embodiment of the sidewall of the battery cover;

DETAILED DESCRIPTION

Figure 1:
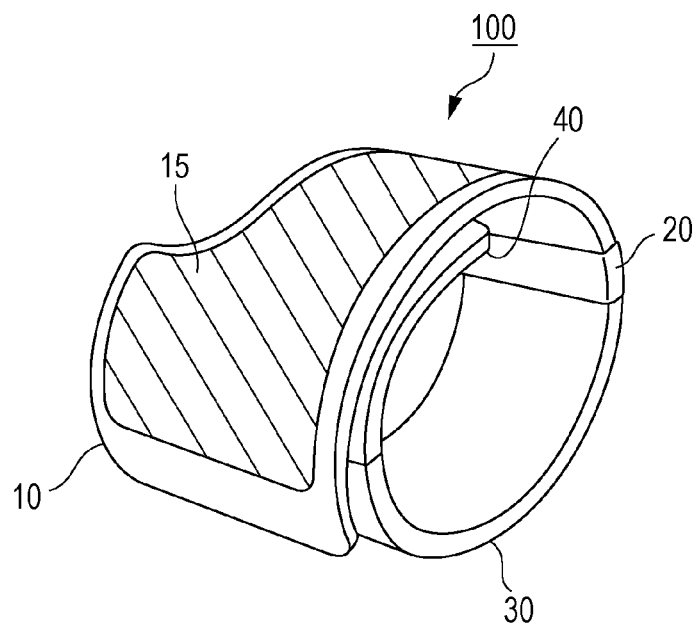
FIG. 1 is an external perspective view of an electronic device according to a first embodiment.

Underlying Knowledge Forming Basis of the Present Disclosure

As described in the description of the related art, wearable multifunction portable terminals, such as arm-wearable electronic devices, are being developed.

In recent years, a user normally operates a portable electronic device via a touch-screen overlying a displaying unit. With regard to an arm-wearable electronic device, it is conceivable that the operability thereof is enhanced by increasing the size (i.e., the length in the circumferential direction) of the displaying unit.

However, when the displaying unit in an electronic device is increased in size, the number of non-flexible portions where the displaying unit is disposed increases, which is a problem in terms of lower fittability.

In contrast, for example, it is conceivable to make the entire electronic device into a flexible elliptical shape or C-shape by using a flexible displaying unit equipped with, for example, an organic electroluminescence (EL) panel and arranging electronic components other than the displaying unit without overlapping (e.g., see Japanese Unexamined Patent Application Publication No. 2007-78670, Japanese Unexamined Patent No. 2008-96543, and Japanese Unexamined Patent Application Publication No. 2005-117224). With this structure, the electronic components may possibly break or deteriorate as a result of, for example, repeated bending.

In order to solve this problem, a wearable an electronic device according to an aspect of the present disclosure includes a first belt, front surface of the first belt being provided with a display having a curved display face; a second belt; a hinge that connects a first end of the first belt to a first end of the second belt. A shape of a space formed by the first belt and the second belt is capable of an elliptical shape when the wearable electronic device worn around a subject is viewed from a side of the wearable electric device. The hinge has higher flexibility than the first belt and the second belt. The wearable electronic device has a first engagement unit that is provided at a second end and a rear surface of the first belt, the second end of the first belt being opposite the first end of the first belt. The first engagement unit is provided in a region of the rear surface of the first belt, in the region, the elliptical shape having smaller curvature than other regions of the elliptical shape. The wearable electronic device has a second engagement unit that is provided at an outer side of the second belt and that engages with the first engagement unit.

In this wearable electronic device, the first belt and the second belt are connected to each other by the hinge having higher flexibility than the first belt and the second belt. Thus, portions with low flexibility within the electronic device can be increased in size. Therefore, the displaying unit can be increased in size, or high functionality can be readily achieved by increasing the number of electronic components disposed within the first belt or the second belt. Furthermore, since a portion with high flexibility can be reduced in size, for example, the risk of damage to a substrate caused by bending can be suppressed. Moreover, by opening and closing the first belt and the second belt about the hinge, a user can readily wear the wearable electronic device.

Furthermore, the space formed by the first belt and the second belt has an elliptical shape so that the electronic device can have a shape similar to the cross-sectional shape of the wrist. Thus, fittability of the wearable electronic device on the arm is improved.

Generally, when the flexible displaying unit is formed by stacking a plurality of displaying elements, such as a touchscreen and a display, a force acts on the flexible displaying unit for restoring its original shape. Therefore, even if the first engagement unit and the second engagement unit of the second belt engage with each other, the first engagement unit may be unable to overcome the force of the flexible displaying unit for restoring its original shape, depending on the position of the first engagement unit disposed in the first belt. Thus, the first engagement unit tends to easily disengage from the second engagement unit. According to this aspect, the first engagement unit is provided at the second end of the first belt that is opposite the first end thereof connected to the hinge and in the region where the substantially elliptical shape has small curvature in the rear surface of the first belt.

By providing the first engagement unit in the region where the elliptical shape has small curvature in this manner, the first engagement unit can engage with the second engagement unit at a location where the first engagement unit can maximally overcome the force of the flexible displaying unit for restoring its original shape. As a result, the tendency of the first engagement unit to easily disengage from the second engagement unit is suppressed, so that a simple and efficient engagement mechanism is achieved. In addition, with the engagement units being disposed at the rear side of the first belt, a wide displaying unit can be provided.

Furthermore, for example, the first belt may be capable of being semielliptical arc shape when the wearable electronic device is viewed from a side of the wearable electronic device, and the second belt may be capable of being semielliptical arc shape when the wearable electronic device is viewed from a side of the wearable electronic device.

Accordingly, the user can readily wear the wearable electronic device. In other words, the wearable electronic device with improved fittability is achieved.

Furthermore, for example, when the wearable electronic device worn around the subject is viewed from the side of the wearable electronic device, the wearable electronic device is divided into a first portion and a second portion by a virtual line extending through a center of the elliptical shape and a middle of the hinge, and the second engagement unit is provided at an outer surface of the second belt within the second portion, the first portion extending from the middle of the hinge to a position where the virtual line intersects with the first belt, the second portion extending from the middle of the hinge to a position where the virtual line intersects with the second belt.

Accordingly, the second engagement unit is provided at a position that allows the second end (i.e., the first engagement unit) of the first belt to bite into the second belt, so that a simple and efficient engagement mechanism is achieved.

Furthermore, for example, one of the first engagement unit and the second engagement unit has guide grooves, the guide grooves being arranged in a circumferential direction of the elliptical shape, and the other one of the first engagement unit and the second engagement unit has projections, the projections being fitted into the guide grooves when the wearable electronic device is worn around the subject.

Accordingly, misalignment between the first engagement unit and the second engagement unit in the width direction can be suppressed when the two engagement units engage with each other.

Furthermore, for example, a third belt having higher flexibility than the first belt and the second belt, the third belt being connected to an edge side of the second engagement unit at a second end of the second belt, the second end of the second belt being opposite the first end of the second belt connected to the hinge. When the electronic device is worn around the subject, the first belt overlaps an outer surface of the third belt.

Accordingly, the third belt having higher flexibility than the first belt is provided at the edge side of the second engagement unit. Therefore, even though the outer surface of the third belt overlaps the first belt, the shape of the third belt conforms to the shape of the first belt. As a result, interference of the third belt with respect to the engagement between the first engagement unit and the second engagement unit is reduced, and the tendency of the first engagement unit to easily disengage from the second engagement unit can be suppressed.

Furthermore, for example, the third belt may include a flexible battery therein.

Accordingly, the flexible battery is disposed within the third belt having higher flexibility than the first belt. Therefore, the battery does not break even when the third belt bends in conformity to the shape of the first belt. Moreover, other non-flexible components can be disposed in the first belt and the second belt while suppressing the tendency of the first engagement unit to easily disengage from the second engagement unit. As a result, the limited space within the first belt and the second belt can be utilized in the most effective manner.

Furthermore, for example, the third belt may include a flexible battery and a cover attached to one of principal surfaces of the flexible battery. The cover may have sidewalls along a side surface of the flexible battery, the side walls extending in a circumferential direction of the elliptical shape. The sidewalls may include a plurality of protrusions that are arranged in the circumferential direction of the elliptical shape, gaps being interposed between each of the plurality of protrusions, and the plurality of protrusions protruding toward another one of the principal surfaces of the flexible battery.

Accordingly, bending of the flexible battery can be regulated to a certain amount.

Furthermore, for example, when the third belt is bent toward the other one of the surfaces of the flexible battery, each of the protrusions contacts with the adjacent one or more of the protrusions.

Accordingly, bending of the flexible battery can be regulated to a certain amount, whereby the flexible battery can be safely protected.

Furthermore, for example, when the cover is viewed from the other one of the surfaces of the flexible battery, each of the gaps may be V-shaped. When the third belt is bent toward the other one of the surfaces of the flexible battery, each of the protrusions may mesh with the adjacent one or more of the protrusions.

Accordingly, since the protrusions mesh with each other, a bending regulation effect can be achieved more reliably.

Furthermore, for example, a bending regulation member is provided in each of the gaps. When the third belt is bent toward the other one of the surfaces of the flexible battery, each bending regulation member may contact with the protrusions adjacent to the bending regulation member.

Accordingly, bending of the flexible battery can be regulated to a certain amount, whereby the flexible battery can be safely protected.

Furthermore, for example, the wearable electronic device may further include a sensor that is provided at the rear surface of the first belt and that contact with the subject when the wearable electronic device is worn around the subject.

Accordingly, load applied to the subject when the sensor contact with the subject can be reduced.

Furthermore, for example, the electronic device may further include a communication unit that is provided in the second belt and that communicates wirelessly with an external device.

Accordingly, the wearable electronic device is capable of communicating wirelessly with an external device (such as a smartphone). Moreover, by bringing the wearable electronic device close to an external device, the electronic device can be used, for example, at a station ticket gate, for making a payment with electronic money, and for identification authentication when entering a building.

Furthermore, for example, the second belt may be provided with a substrate equipped with a circuit, and the hinge may be provided with a flexible substrate that connects the display to the substrate.

Accordingly, a rigid substrate equipped with a circuit element can be electrically connected to the displaying unit by the flexible substrate.

Furthermore, for example, the wearable electronic device may further include a battery, the first belt has the battery at a position other than a position where the displaying unit is provided in the first belt.

Accordingly, by disposing the displaying unit and the battery without overlapping, the electronic device can be reduced in thickness.

Embodiments of the present disclosure will be described below with reference to the drawings. The embodiments described below indicate specific examples of the present disclosure. Numerical values, shapes, materials, components, positions and connection methods of components, steps, the order of steps, and so on in the following embodiments are examples and are not intended to limit the present disclosure.

Furthermore, of the components in the following embodiments, components that are not defined in the independent claim indicating the broadest concept are described as arbitrary components. The drawings are schematic diagrams and are not necessarily exact. Therefore, there are sections that do not exactly match between the drawings.

First Embodiment

Overall Configuration

Figure 2:
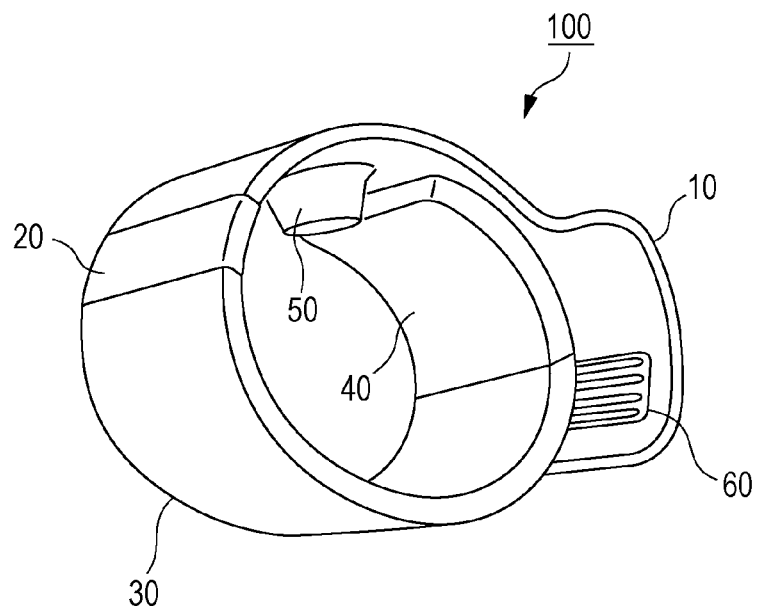
FIG. 2 is an external perspective view of the electronic device according to the first embodiment.
Figure 3:
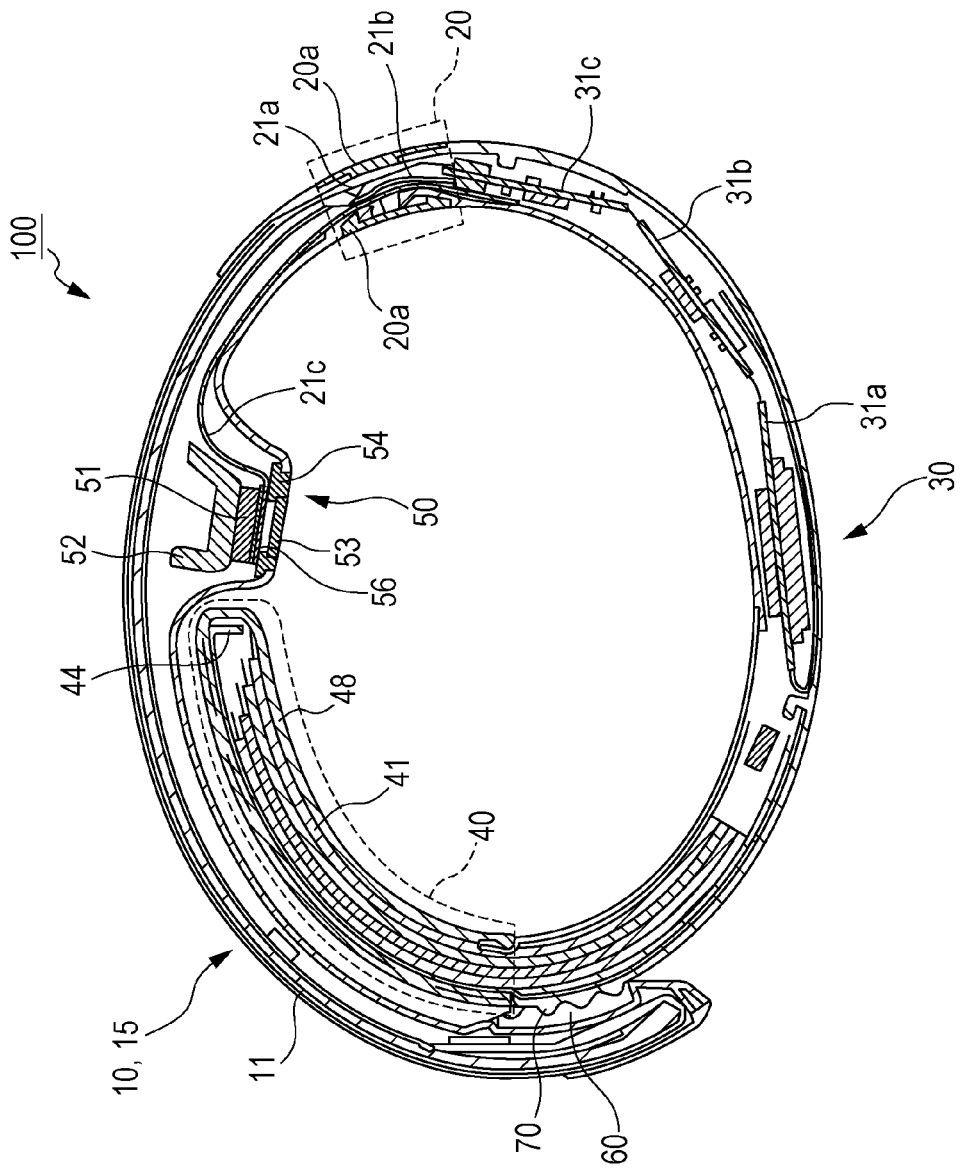
FIG. 3 is a cross-sectional view of the electronic device according to the first embodiment, as viewed from the side.

First, the overall configuration of an electronic device according to a first embodiment will be described. FIGS. 1 and 2 are external perspective views of the electronic device according to the first embodiment. FIG. 3 is a cross-sectional view of the electronic device according to the first embodiment, as viewed from the side.

As shown in FIGS. 1 to 3, an electronic device 100 includes a first belt 10, a second belt 30, a hinge 20, a third belt 40, and a sensor unit 50.

The electronic device 100 is an arm-wearable electronic device. The electronic device 100 has, for example, a function for measuring the pulse rate of a user wearing the electronic device 100, a clock function, and a function for linking with a smartphone. In the following description, a surface facing a subject (user's wrist) when the electronic device 100 is worn around the subject will be referred to as "inner surface".

The first belt 10 is a non-flexible belt whose front surface is provided with a displaying unit 15 having a curved display face. In the first embodiment described below, the term "non-flexible" means that the first belt 10 is substantially non-bendable but does not necessarily mean that the first belt 10 does not bend at all. In other words, the first belt 10 does not have flexibility as a belt. The first belt 10 at least has lower flexibility (i.e., is more rigid) than the hinge 20.

Specifically, the first belt 10 is a hollow-plate-shaped member composed of rigid acrylonitrile-butadiene-styrene (ABS) resin and is substantially semielliptical-shaped (i.e., substantially C-shaped) when viewed from the side of the electric device 100.

The material used for the first belt 10 is not particularly limited and may be other rigid resin, such as polycarbonate resin or engineering plastic. Furthermore, the first belt 10 may partially or entirely be formed of a metallic member or a ceramic member.

An organic electroluminescence (EL) panel 11 and a touch-screen that constitute the displaying unit 15 are provided within the first belt 10. Accordingly, if the first belt 10 does not have flexibility in its entirety, a flexible member may be provided within the first belt 10. Although not shown in detail, the first belt 10 is actually constituted of a combination of a plurality of members.

A first end of the first belt 10 is connected to the hinge 20. A second end of the first belt 10 overlaps the outer surface of the second belt 30 when the electronic device 100 is worn around the subject (sometimes referred to as "worn state" hereinafter). Furthermore, when in the worn state, the first belt 10 overlaps the outer surface of the third belt 40.

The inner surface of the second end of the first belt 10 (i.e., an area of the first belt 10 that faces the second belt 30 when in the worn state) is provided with a first engagement unit 60.

The second belt 30 is a non-flexible belt. Specifically, as shown in FIGS. 1 to 3, the second belt 30 is a hollow-plate-shaped member composed of rigid ABS resin and is substantially semielliptical-shaped (i.e., substantially C-shaped) when viewed from the side of the electric device 100.

The material used for the second belt 30 is not particularly limited and may be other rigid resin, such as polycarbonate resin or engineering plastic. Furthermore, the second belt 30 may partially or entirely be formed of a metallic member or a ceramic member.

The second belt 30 is provided therein with a rigid substrate 31a, a rigid substrate 31b, and a rigid substrate 31c, each of which has circuit elements (such as a resistor, a capacitor, and an integrated circuit) mounted therein. The substrate 31a and the substrate 31b are connected to each other via a flexible substrate, and the substrate 31b and the substrate 31c are connected to each other via a flexible substrate. Furthermore, a part of a battery 41 is provided within the second belt 30. The battery 41 is disposed within the second belt 30 such that the battery 41 does not overlap the displaying unit 15 when a user wears the electronic device 100 around his/her arm. Alternatively, the battery 41 may be disposed within the first belt 10 so long as the position of the battery 41 does not overlap the displaying unit 15 of the first belt 10. Although not shown in detail, the second belt 30 is actually constituted of a combination of a plurality of members.

A first end of the second belt 30 is connected to the hinge 20. A second end of the second belt 30 is connected to the third belt 40. When in the worn state, the second end of the first belt 10 overlaps the outer surface of the second end of the second belt 30.

The outer surface of the second end of the second belt 30 (i.e., an area of the second belt 30 that faces the first belt 10 when in the worn state) is provided with a second engagement unit 70.

The hinge 20 is a flexible portion (connection portion) that connects the first end of the first belt 10 to the first end of the second belt 30. A shape formed by the first belt 10 and the second belt 30 is a substantially elliptical shape when the electronic device 100 worn around the subject is viewed from the side of the wearable electronic device. In the first embodiment, the term "flexible" means that an object is substantially bendable. The hinge 20 has higher flexibility than either of the first belt 10 or the second belt 30.

The hinge 20 is mainly constituted of a tubular cover 20a composed of silicon rubber. In other words, the hinge 20 is a part of a belt (i.e., the electronic device 100) having a hinge function for the first belt 10 and the second belt 30, and does not necessarily need to be structurally hinge-shaped.

A part of a flexible substrate 21a and a part of a flexible substrate 21b, which connect the organic EL panel 11 to the substrate 31c, and a part of a flexible substrate 21c, which connects a sensor substrate 56 (i.e., a substrate equipped with a pulse-wave sensor (not shown)) within the sensor unit 50 to the substrate 31c are provided within the hinge 20.

Accordingly, although the hinge 20 is desirably constituted of flexible members, the hinge 20 may include a non-flexible member. In other words, the hinge 20 may have other configurations so long as the hinge 20 has flexibility in its entirety.

The third belt 40 is a flexible belt that is connected to an edge side of the second engagement unit 70 at the second end of the second belt 30 that is opposite the first end thereof connected to the hinge 20. The third belt 40 is mainly constituted of a closed-end tubular cover 48 composed of elastomer (such as silicon rubber or urethane rubber).

The third belt 40 includes therein the battery 41, which has flexibility, and a cover 44 that covers the outer surface of the battery 41. In order to make a bending regulation function, to be described later, more effective, the cover 44 is composed of rigid resin, such as ABS resin, with reduced thickness and increased flexibility. Therefore, the cover 44 has flexibility.

In other words, the third belt 40 is constituted of flexible members and has flexibility in its entirety. The third belt 40 has higher flexibility than either of the first belt 10 or the second belt 30.

When in the worn state, the outer surface of the third belt 40 overlaps the inner surface of the first belt 10. More specifically, when in the worn state, the third belt 40 is disposed on the periphery of the inner surface of the first belt 10 at a position between the first engagement unit 60 and the sensor unit 50.

The sensor unit 50 is provided at the rear surface of the first belt 10 in an area thereof that contacts with the subject when the electronic device 100 is worn around the subject. The sensor unit 50 may be provided as a part of the first belt 10 or may be a separate flexible member, such as elastomer, attached to the inner surface of the first belt 10, like a sensor unit 50a to be described later.

The sensor substrate 56 equipped with the pulse-wave sensor and a sensor holder 52 that holds the sensor substrate 56 via a cushion member 51 are provided within the sensor unit 50. Although the sensor unit 50 is also provided with a lens 53 and a lens holder 54, detailed descriptions thereof will be omitted.

In the first embodiment, the first belt 10, the second belt 30, the hinge 20, and the third belt 40 constitute the entire electronic device 100. Alternatively, a configuration equipped with a belt other than these belts is also permissible. Furthermore, in the first embodiment, although the organic EL panel 11 is used as the displaying unit 15, other kinds of display panels (display means), such as a liquid-crystal panel, may be used as an alternative.

Attachment-Detachment Method

Figure 4A:
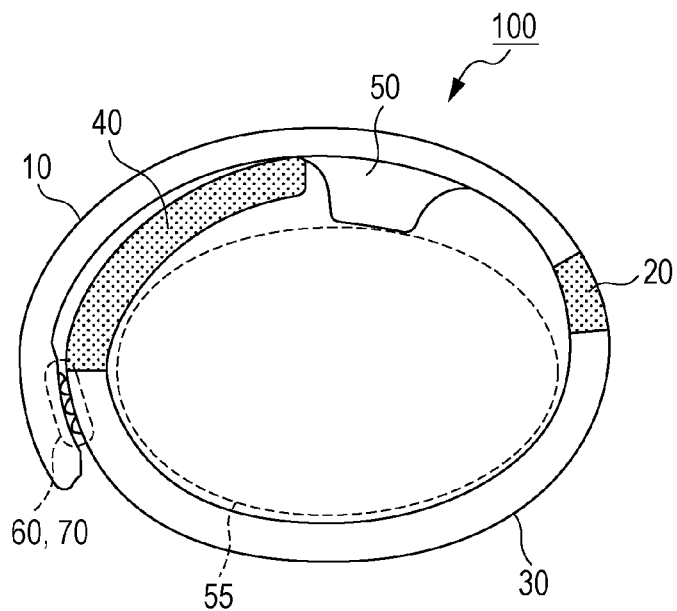
FIG. 4A schematically illustrates how the electronic device according to the first embodiment is attached and detached.
Figure 4B:
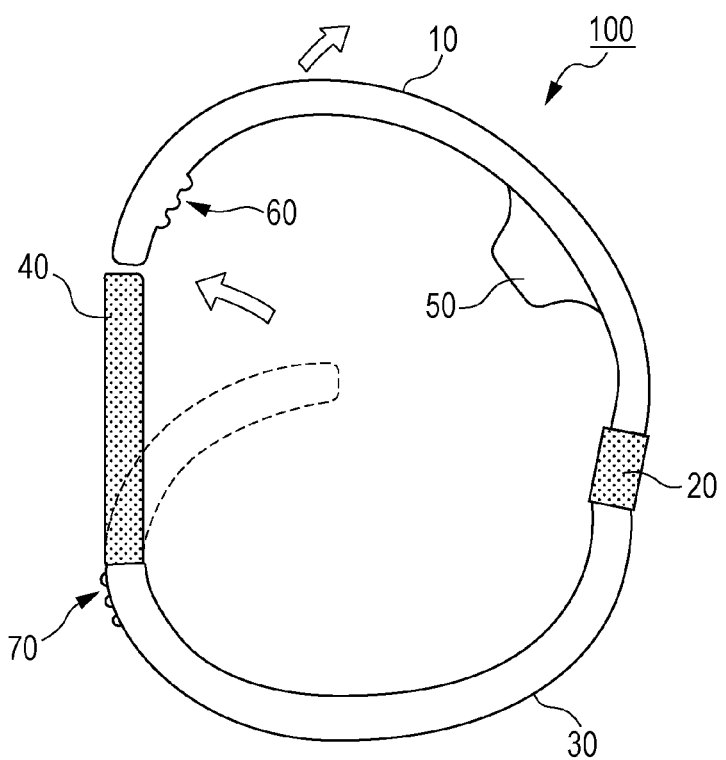
FIG. 4B schematically illustrates how the electronic device according to the first embodiment is attached and detached.

Next, a method for attaching and detaching the electronic device 100 will be described. FIGS. 4A and 4B schematically illustrate how the electronic device 100 is attached and detached. FIG. 4A illustrates a state where the electronic device 100 is worn around a subject 55. FIG. 4B illustrates the attachment-detachment process of the electronic device 100, that is, a state where the electronic device 100 is being detached from the subject 55 as well as a state where the electronic device 100 is being attached to the subject 55.

As shown in FIG. 4A, when the electronic device 100 is worn around the subject 55, the first engagement unit 60 and the second engagement unit 70 are engaged with each other. In a normal state (i.e., a state where stress is not received from another member), the third belt 40 has a tabular shape. However, due to having flexibility, the third belt 40 in the state shown in FIG. 4A is bent by being pressed by the inner surface of the first belt 10. In FIG. 4A, the third belt 40 is located on the periphery of the inner surface of the first belt 10 and is disposed between the first engagement unit 60 and the sensor unit 50. Furthermore, the third belt 40 is disposed between the edge side of the second engagement unit 70 and the sensor unit 50.

In contrast, during the attachment-detachment process of the electronic device 100, as shown in FIG. 4B, the first engagement unit 60 and the second engagement unit 70 are disengaged from each other. Thereby the first belt 10 and the second belt 30 are opened with the flexible hinge 20 acting as a fulcrum.

In this case, as shown in FIG. 4B, since the third belt 40 comes out of contact with the first belt 10, the third belt 40 recovers its tabular shape and tilts outward. Therefore, when the electronic device 100 is to be detached (or attached), the inside of the electronic device 100 opens widely.

As described above, with the configuration in which the non-flexible first belt 10 and the non-flexible second belt 30 are connected to each other by the flexible hinge 20, the user can readily attach or detach the electronic device 100 to or from himself/herself by simply opening and closing the first belt 10 and the second belt 30 using the hinge 20 as a fulcrum.

Generally, battery space is often a problem when reducing the size of an electronic device. In the electronic device 100, the flexible battery 41 is provided within the third belt 40, which corresponds to an end of the entire electronic device 100. Therefore, with the electronic device 100, the battery 41 does not interfere with the attachment-detachment process, and space for incorporating other circuit components can be ensured within the nonflexible first belt 10 and the nonflexible second belt 30.

Arrangement of Engagement Units

Figure 5:
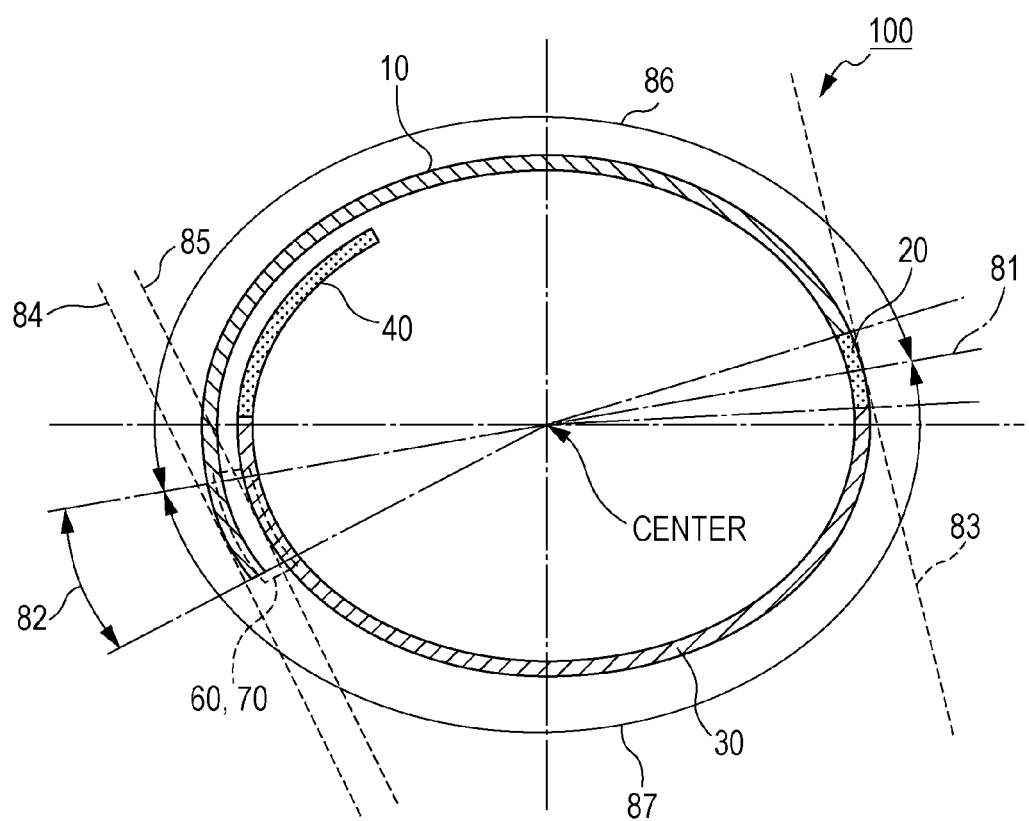
FIG. 5 schematically illustrates the arrangement of a first engagement unit and a second engagement unit.

Next, the arrangement of the first engagement unit 60 and the second engagement unit 70 will be described. FIG. 5 schematically illustrates the arrangement of the first engagement unit 60 and the second engagement unit 70. Specifically, FIG. 5 schematically illustrates the electronic device 100 in the worn state, as viewed from the side of the electric device 100. In FIG. 5, the sensor unit 50 is not shown.

In the electronic device 100, the second engagement unit 70 is provided at a position that allows the first engagement unit 60 to bite into the second belt 30 so that the first engagement unit 60 and the second engagement unit 70 can readily engage with each other during the wearing process.

Specifically, as shown in FIG. 5, the first engagement unit 60 is provided at the inner surface of the first belt 10 located within a range 82. The second engagement unit 70 is provided at the outer surface of the second belt 30 located within the range 82.

As shown in FIG. 5, when the electronic device 100 in the worn state is viewed from the side, the range 82 is located between a virtual line 81 and a line (i.e., a line component). The virtual line 81 extends through the center of the elliptical shape (substantially elliptical shape) and the middle of the hinge 20 in the circumferential direction. The line (i.e., a line component) connects the aforementioned center and the second end (i.e., the edge of the second end) of the first belt 10.

The electronic device 100 is divided into a first portion 86 and a second portion 87 by the line 81. The line 81 extends through the center of the elliptical shape (substantially elliptical shape) formed by the first belt 10 and the second belt 30 and the middle of the hinge 20 in the circumferential direction. In the electronic device 100, the first portion 86 extends from the middle of the hinge 20 in the circumferential direction to a position where the line 81 intersects with the first belt 10. In the electronic device 100, the second portion 87 extends from the middle of the hinge 20 in the circumferential direction to a position where the line 81 intersects with the second belt 30. Although an ellipse that constitutes the first portion 86 and an ellipse that constitutes the second portion 87 may be identical shapes, the two ellipses do not necessarily have to be identical shapes.

When regulating the position of the first engagement unit 60 by using the first portion 86 and the second portion 87, it can be said that the first engagement unit 60 is provided at the inner surface of the first belt 10 included in the second portion 87. Likewise, it can be said that the second engagement unit 70 is provided at the outer surface of the second belt 30 included in the second portion 87.

Furthermore, a tangent line 83 at the middle (i.e., the axis of opening and closing) of the hinge 20 in the circumferential direction and a tangent line (e.g., a tangent line 84) at the outer (or inner) surface of the first belt 10 located within the range 82 intersect with each other at the second portion 87 side. Likewise, the tangent line 83 and a tangent line 85, the tangent line 85 being at the outer (or inner) surface of the second belt 30 located within the range 82, intersect with each other at the second portion 87 side.

By arranging the first engagement unit 60 and the second engagement unit 70 in this manner, a simple and efficient engagement mechanism that allows the first engagement unit 60 and the second engagement unit 70 to readily engage with each other during the wearing process is achieved.

As will be described later, the first engagement unit 60 and the second engagement unit 70 are normally formed of protrusions. By arranging the first engagement unit 60 and the second engagement unit 70 in the above-described manner, the protrusions can be reduced in height. Thus, smooth opening and closing of the first belt 10 and the second belt 30 can be performed.

Configurations of Engagement Units

Figure 6A:
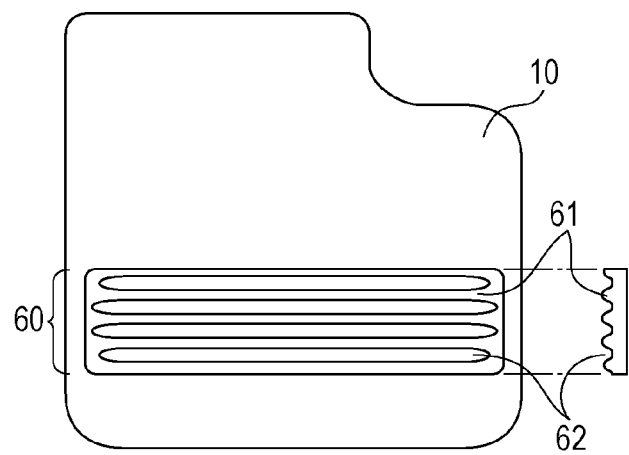
FIG. 6A schematically illustrates a specific configuration of the first engagement unit.
Figure 6B:
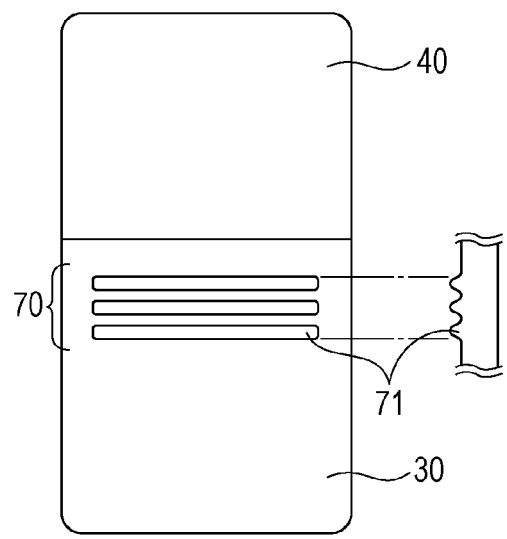
FIG. 6B schematically illustrates a specific configuration of the second engagement unit.

Next, specific configurations of the first engagement unit 60 and the second engagement unit 70 will be described. FIGS. 6A and 6B schematically illustrate specific configurations of the first engagement unit 60 and the second engagement unit 70.

FIG. 6A illustrates the first engagement unit 60 provided at the inner surface of an end of the first belt 10. The first engagement unit 60 has a plurality of (five in FIG. 6A) protrusions 61 extending in the width direction of the first belt 10 and recesses 62 formed between the protrusions 61.

FIG. 6B illustrates the second engagement unit 70 provided at the outer surface (i.e., front surface) of the second belt 30. The second engagement unit 70 has a plurality of (three in FIG. 6B) protrusions 71 extending in the width direction of the second belt 30.

The first engagement unit 60 and the second engagement unit 70 are composed of rigid resin, such as ABS resin. Alternatively, the first engagement unit 60 and the second engagement unit 70 may be composed of a highly-abrasion-resistant material, such as polyacetal.

As a further alternative, the first engagement unit 60 and the second engagement unit 70 may be composed of elastomer. Because a material with high friction force like elastomer is suitable for engagement, such a material can be used for the first engagement unit 60 and the second engagement unit 70. Furthermore, the first engagement unit 60 and the second engagement unit 70 may be composed of different materials. For example, one of the first engagement unit 60 and the second engagement unit 70 may be composed of elastomer, whereas the other one may be composed of rigid resin.

When the electronic device 100 is to be worn, the protrusions 71 engage with the protrusions 61 (and the recesses 62). In this case, position adjustment is possible during the wearing process by shifting the engagement position in the circumferential direction of the electronic device 100 (i.e., a direction orthogonal to the width direction of the electronic device 100).

It is conceivable that the first engagement unit 60 and the second engagement unit 70 become engaged in a misaligned manner in the width direction during the wearing process of the electronic device 100. In order to suppress such misalignment in the width direction, one of the first engagement unit 60 and the second engagement unit 70 may be provided with a guide groove.

Figure 7A:
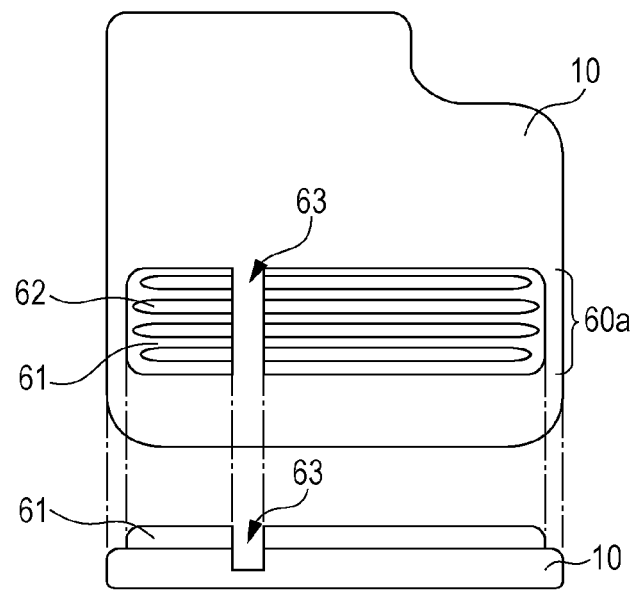
FIG. 7A schematically illustrates a specific configuration of a first engagement unit provided with a guide groove.
Figure 7B:
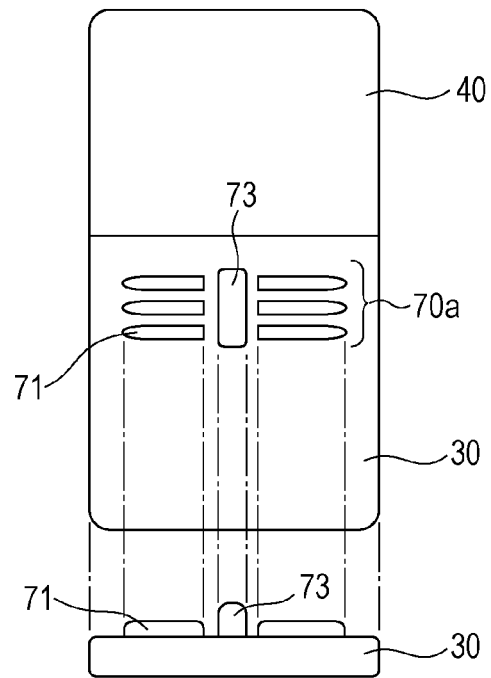
FIG. 7B schematically illustrates a specific configuration of a second engagement unit.

FIGS. 7A and 7B illustrate specific configurations of the first engagement unit 60 and the second engagement unit 70 that are provided with guide grooves.

FIG. 7A illustrates a first engagement unit 60a provided at the inner surface of an end of the first belt 10. The first engagement unit 60a has a plurality of protrusions 61 extending in the width direction of the first belt 10, recesses 62 formed between the protrusions 61, and a guide groove 63 arranging in the circumferential direction of the substantially elliptical shape.

FIG. 7B illustrates a second engagement unit 70a provided at the outer surface (i.e., front surface) of the second belt 30. The second engagement unit 70a has a plurality of protrusions 71 extending in the width direction of the second belt 30 and a projection 73.

When the electronic device 100 is to be worn, the protrusions 71 do not engage with the recesses 62 unless the projection 73 is fitted into the guide groove 63. Therefore, with this configuration, misalignment of the engagement position of the first engagement unit 60a and the second engagement unit 70a in the width direction can be suppressed.

A similar effect can be achieved by providing a guide groove in the second engagement unit 70 and providing a projection, which is to be fitted into the guide groove, in the first engagement unit 60.

Although the configurations of the first engagement unit 60 and the second engagement unit 70 have been described above, the configurations of the first engagement unit 60 and the second engagement unit 70 are not limited to such configurations. The first engagement unit 60 and the second engagement unit 70 may have any configurations that allow them to be engaged with each other during the wearing process.

Figure 8:
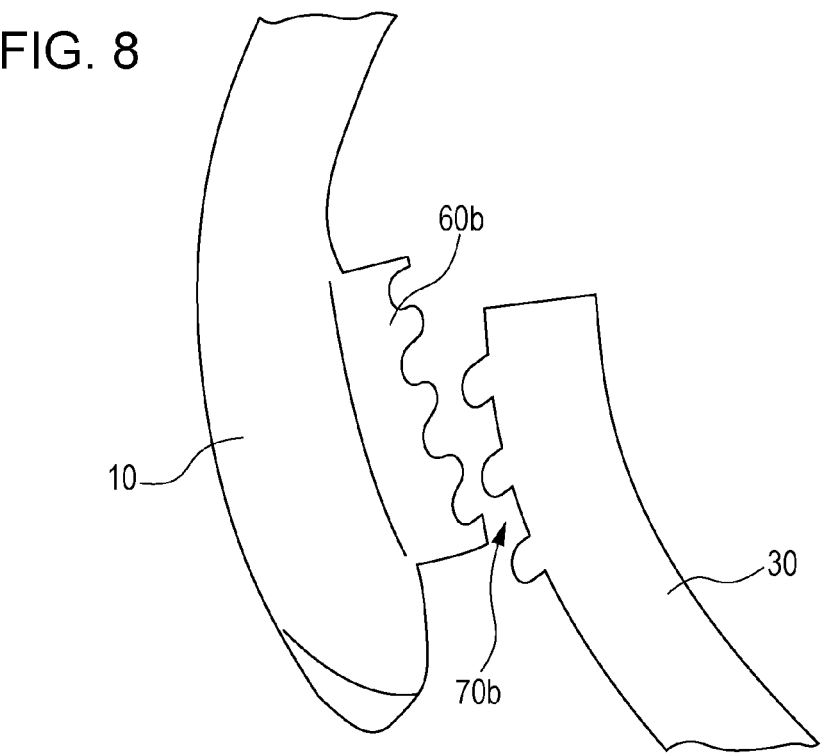
FIG. 8 illustrates specific configurations of a first engagement unit and a second engagement unit that have tilted protrusions.

For example, in order to achieve improved engageability, the protrusions 61 (and the recesses 62) and the protrusions 71 may be tilted. FIG. 8 illustrates specific configurations of a first engagement unit 60b and a second engagement unit 70b that have tilted protrusions, as viewed from the side of the electric device 100.

As shown in FIG. 8, the protrusions of the second engagement unit 70b engage with the protrusions (and the recesses) of the first engagement unit 60b. With regard to the protrusions of the first engagement unit 60b and the protrusions of the second engagement unit 70b, in a case where the first belt 10 and the second belt 30 are to be opened about the hinge 20, the protrusions of the second engagement unit 70b are tilted in a direction for engaging with the recesses of the first engagement unit 60b.

With this configuration, the first engagement unit 60b and the second engagement unit 70b can engage with each other more securely, thereby reducing the risk of the electronic device 100 falling off unintentionally from user's arm.

Bending Regulation Structure 1 of Battery

Figure 9:
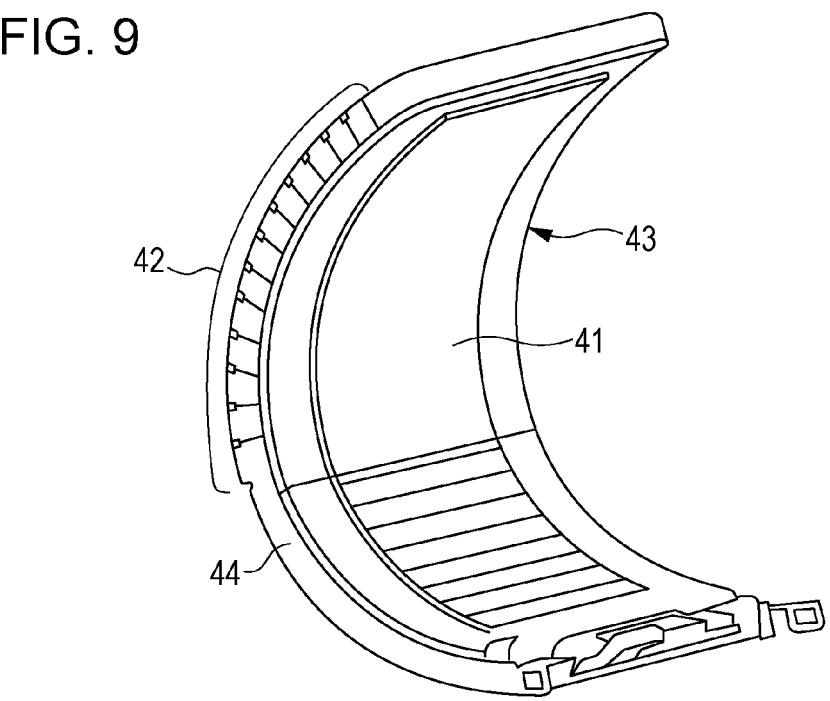
FIG. 9 schematically illustrates a first embodiment of a sidewall of a battery cover.
Figure 10:
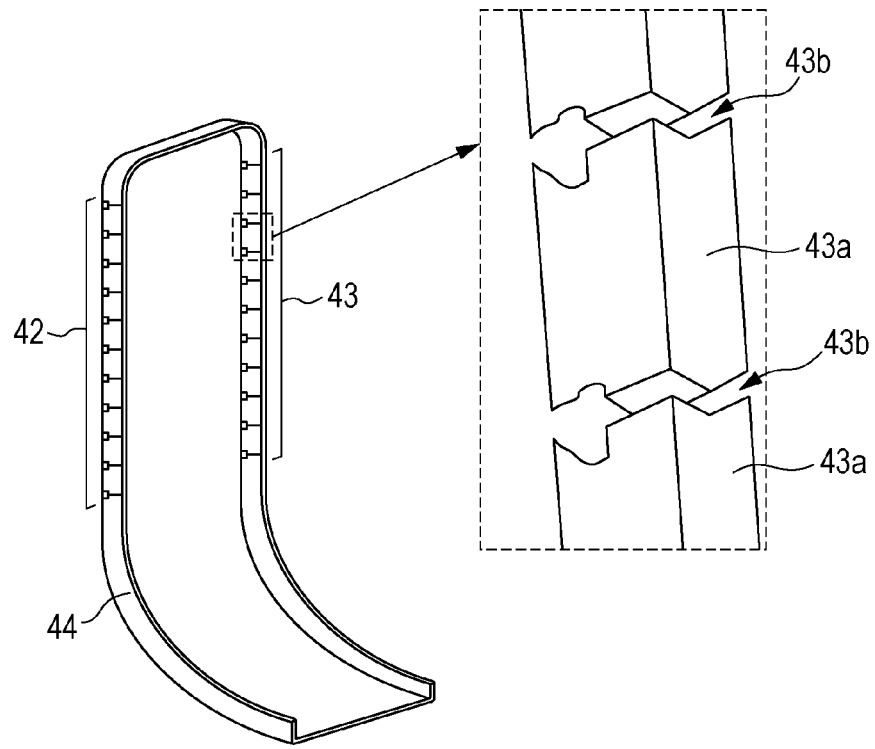
FIG. 10 illustrates the external appearance of the battery cover.

The battery 41 included in the third belt 40 has flexibility but may possibly break if bent beyond its limit. In the electronic device 100, a sidewall of the cover 44 has a structure that regulates inward bending of the battery 41 to a certain amount. FIG. 9 schematically illustrates a first embodiment of the sidewall of the cover 44 for the battery 41 and shows a state where the battery 41 is inwardly bent. FIG. 10 illustrates the external appearance of the cover 44 for the battery 41.

As shown in FIG. 9, the cover 44 is attached to the outer surface of the battery 41. As described with reference to FIG. 3, in actuality, the third belt 40 is configured such that the battery 41 whose outer surface is covered with the cover 44 is further accommodated within the cover 48. However, in FIG. 9, the cover 48 is not shown.

As shown in FIGS. 9 and 10, the cover 44 has a sidewall 42 and a sidewall 43 that extend in the circumferential direction along the side surfaces of the battery 41. Although only the sidewall 43 will be described in detail below, the sidewall 42 has a configuration similar to that of the sidewall 43.

The sidewall 43 is constituted of a plurality of protrusions 43a arranged in the circumferential direction of the substantially elliptical shape, gaps 43b being interposed between each of the plurality of protrusions. The plurality of protrusions 43a protrude toward the inner surface (exposed surface) of the battery 41. With the sidewall 43 having this configuration, when the battery 41 (and the third belt 40) is bent inwardly as shown in FIG. 10, each protrusion 43a contacts with the protrusions 43a adjacent to the protrusion 43a, so that the battery 41 is prevented from being inwardly bent by a certain amount or more.

Furthermore, when the cover 44 is viewed from the inner side, the gaps 43b are V-shaped. When the battery 41 (and the third belt 40) is inwardly bent, each protrusion 43a meshes with the protrusions 43a adjacent to the protrusion 43a.

If the battery 41 is largely bent, it is conceivable that the bending regulation effect is not achievable due to misalignment of the protrusions 43a constituting the sidewall 43 in the width direction. However, since the V-shaped gaps 43b allow each protrusion 43a to mesh with the adjacent protrusions 43a, the bending regulation effect can be achieved more reliably.

Figure 11:
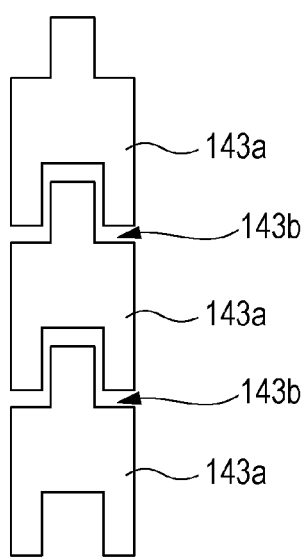
FIG. 11 illustrates the configuration of another embodiment of a sidewall of a battery cover.

The shape of each gap 43b is only an example and may be other shapes. FIG. 11 illustrates the configuration of another embodiment of the sidewall of the cover 44 for the battery 41. FIG. 11 shows a conceivable configuration in which gaps 143b having a convex shape allow adjacent protrusions 143a to mesh with each other when the battery 41 (and the third belt 40) is inwardly bent.

If outward bending of the battery 41 is to be regulated, the cover 44 may be attached to the inner surface of the battery 41 (such that the protrusions 43a protrude outward). In other words, when the cover 44 is attached to one of the principal surfaces of the battery 41, bending of the battery 41, disposed in the third belt 40, toward the other principal surface can be regulated.

Bending Regulation Structure 2 of Battery

Figure 12:
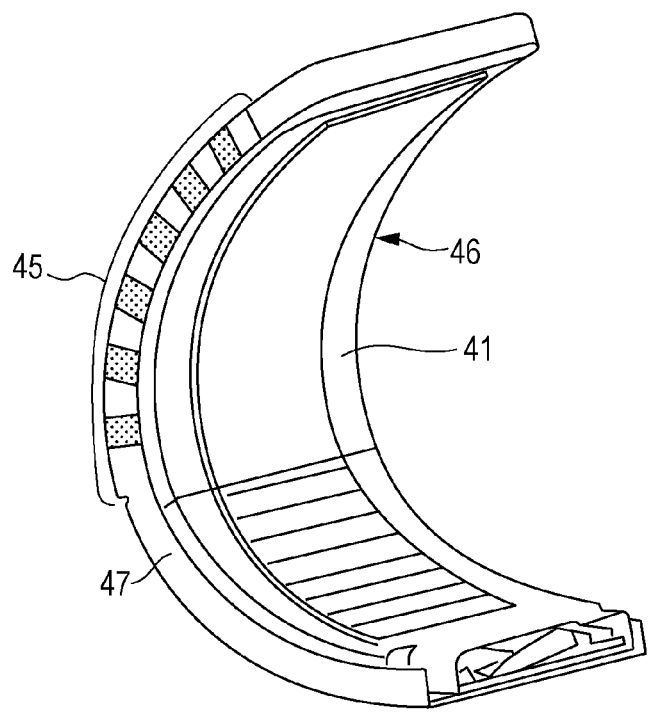
FIG. 12 schematically illustrates a second embodiment of a sidewall of a battery cover.

The structure that regulates inward bending of the battery 41 to a certain amount may alternatively be the following structure. FIG. 12 schematically illustrates a second embodiment of a sidewall of a cover for the battery 41 and shows a state where the battery 41 is inwardly bent. FIGS. 13A and 13B illustrate the configuration of the second embodiment of the sidewall of the cover for the battery 41.

As shown in FIG. 12, a cover 47 covers the outer surface of the battery 41. The cover 47 has a sidewall 45 and a sidewall 46 that extend in the circumferential direction of the substantially elliptical shape along the side surfaces of the battery 41. Although only the sidewall 45 will be described in detail below, the sidewall 46 has a configuration similar to that of the sidewall 45.

As shown in FIGS. 13A and 13B, the sidewall 45 has gaps 45g arranged and spaced apart from each other in the circumferential direction of the substantially elliptical shape. The sidewall 45 includes a plurality of protrusions 45a protruding toward the inner surface (exposed surface) of the battery 41 and bending regulation members 45b provided in the gaps

45g. More specifically, the plurality of protrusions 45a are each provided with a groove 45e extending in the circumferential direction of the substantially elliptical shape. Tabular portions 45d of the bending regulation members 45b are fitted within the grooves 45e.

When the battery 41 (and the third belt 40) is inwardly bent, each bending regulation member 45b contacts with the protrusions 45a adjacent to the bending regulation member 45b, so that the battery 41 is prevented from being inwardly bent by a certain amount or more. Specifically, corners 45c of the protrusions 45a contacts with surfaces 45f of the bending regulation members 45b. Thereby the battery 41 is prevented from being inwardly bent by a certain amount or more.

Furthermore, with the sidewall 45 having this configuration, the tabular portions 45d of the bending regulation members 45b are fitted within the grooves 45e of the protrusions 45a. Therefore, the bending regulation effect can be reliably achieved without the protrusions 45a and the bending regulation members 45b being misaligned with each other in the width direction.

Moreover, with this configuration in which separate components, such as the bending regulation members 45b, are fitted between adjacent protrusions 45a, the following effect can be achieved by processing the bending regulation members 45b.

For example, by preliminarily processing the surfaces 45f of the bending regulation members 45b such that the contact area between the protrusions 45a and the surfaces 45f increases when the battery 41 is bent, the material rigidity of the sidewall 45 can be reduced. Therefore, an inexpensive, readily-processable material, such as resin, can be used for the bending regulation members 45b.

Furthermore, the protrusions 45a can be fabricated inexpensively by pressing a thin metal plate, such as spring stainless steel. This allows for a further increase in strength as compared with the protrusions 45a composed of resin.

Furthermore, by adjusting the angle of the surfaces 45f of the bending regulation members 45b, bending-angle adjustment becomes possible to a certain extent.

Moreover, this configuration in which separate components, such as the bending regulation members 45b, are fitted between adjacent protrusions 45a is advantageous in that each bending regulation member 45b alone can be replaced when the component deteriorates.

Alternative Configuration of Sensor Unit

Figure 14A:
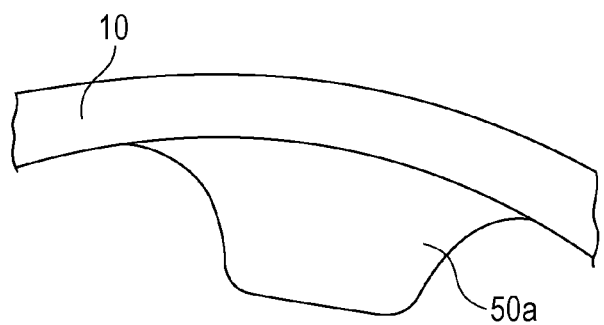
FIG. 14A schematically illustrates a flexible sensor unit.
Figure 14B:
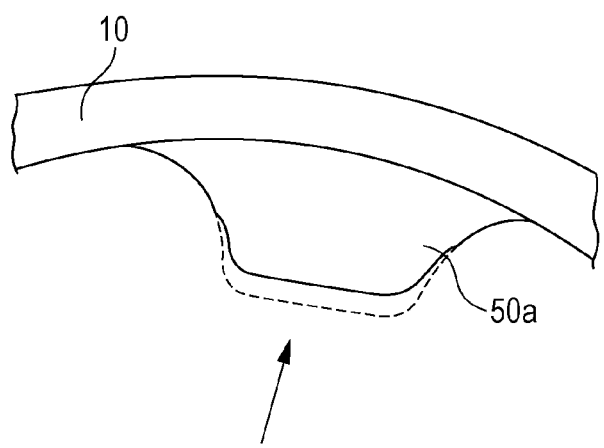
FIG. 14B schematically illustrates the flexible sensor unit.

Although the sensor unit 50 is described as being non-flexible in the above embodiment, the sensor unit 50 may be constituted of a separate flexible member and may be provided at the inner surface (rear surface) of the first belt 10. FIGS. 14A and 14B schematically illustrate a flexible sensor unit.

As shown in FIGS. 14A and 14B, a sensor unit 50a has flexibility or elasticity. This means that an outer portion of the sensor unit 50a excluding the lens 53 and the lens holder 54 shown in FIG. 3 has flexibility or elasticity.

The outer portion of the sensor unit 50a is composed of, for example, elastomer, such as silicon rubber. As shown in FIGS. 14A and 14B, when the sensor unit 50a is pressed, the sensor unit 50a recedes inward. The sensor holder 52 within the sensor unit 50a may also be composed of a flexible material (e.g., elastomer).

When the outer portion of the sensor unit 50a is pressed, the position of the sensor substrate 56 (pulse-wave sensor) provided within the sensor unit 50a also shifts. The sensor substrate 56 is held by the sensor holder 52 via the cushion member 51 composed of a foamable resin material, such as urethane foam. The sensor substrate 56 is connected to the substrate 31c by the flexible substrate 21c. Therefore, the sensor substrate 56 is capable of following the movement of the sensor unit 50a.

Accordingly, with the outer portion of the sensor unit 50a being constituted of a flexible or elastic member, load applied to user's wrist when the sensor unit 50a contacts with user's wrist can be reduced.

Furthermore, with the outer portion of the sensor unit 50a being constituted of a flexible or elastic member, the lens 53 of the sensor unit 50a comes into close contact with user's wrist. Therefore, the lens 53 is less likely to become positionally displaced relative to the wrist. By reducing positional displacement of the lens 53 relative to the wrist, the pulse-wave sensor can stably measure pulse waves.

Because the displaying unit 15 is provided at the front surface of the first belt 10, the inner side of the first belt 10 normally contacts with the backhand side of user's wrist.

Generally, with regard to measurement of pulse waves using a pulse-wave sensor, sensitivity is higher at the palm side of user's wrist. However, the sensitivity at the palm side of the wrist varies significantly depending on the contact location of the sensor unit 50a. On the other hand, although the backhand side of the wrist provides lower sensitivity than the palm side of the wrist, there is less variation in sensitivity among different contact locations of the sensor unit 50a. In other words, with the sensor unit 50a (sensor unit 50) being provided at the inner side of the first belt 10, the electronic device 100 can stably measure user's pulse waves.

The sensor unit can be given flexibility or elasticity by any method, such as making the sensor unit into a bellows shape by using a flexible member.

Communication Unit

Figure 15:
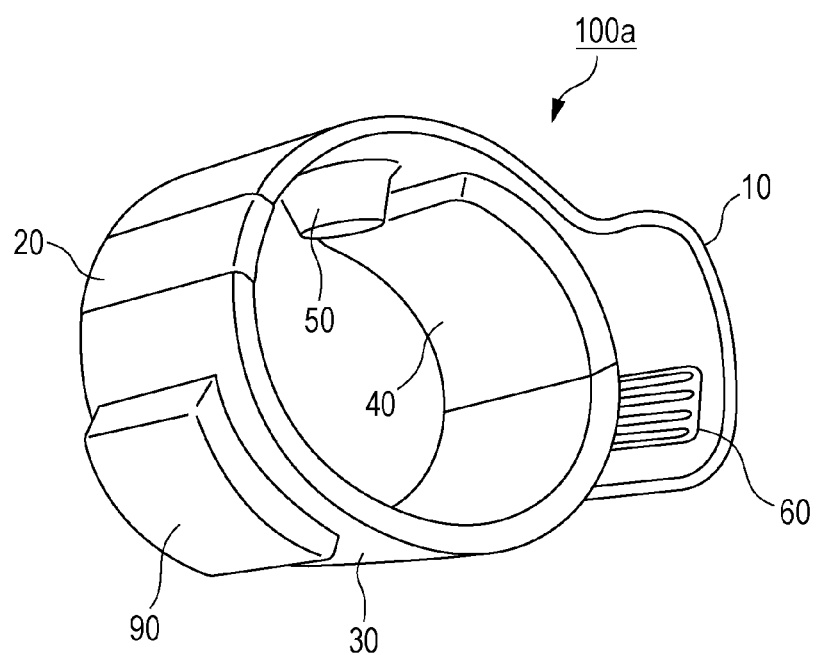
FIG. 15 is an external perspective view of an electronic device equipped with a communication unit.

The electronic device 100 may include a communication unit that communicates wirelessly with an external device. FIG. 15 is an external perspective view of an electronic device 100a equipped with a communication unit.

The electronic device 100a shown in FIG. 15 includes a communication unit 90 provided at the front surface of the second belt 30.

A wireless module (near-field-communication (NFC) tag) of an NFC standard, which is one of radio-frequency-identification (RFID) standards, and a peripheral circuit are provided within the communication unit 90.

The communication unit 90 is provided in the second belt 30 that contacts with the palm side of user's wrist.

The NFC tag is capable of exchanging information with another NFC-compliant external device (e.g., smartphone) by being brought close to the external device, and is used, for example, at a station ticket gate, for making a payment with electronic money, and for identification authentication when entering a building. The communication unit 90 is provided in the second belt 30 located at user's palm side. With this structure, the electronic device 100a can be readily brought close to (held over) an external device.

The wireless module provided in the communication unit 90 is not limited to the NFC tag and may alternatively be a wireless module that communicates wirelessly with an external device via, for example, Bluetooth (registered trademark) or Wi-Fi (registered trademark).

The electronic device according to the present disclosure may include the following alternative embodiments.

An wearable electronic device according to another embodiment of the present disclosure includes a first belt provided with a displaying unit, a second belt, and a hinge that connects a first end of the first belt to a first end of the second belt and that has higher flexibility than the first belt and the second belt. When the wearable electronic device is worn around a subject, a second end of the first belt overlaps an outer surface of the second belt.

In this electronic device, since portions with low flexibility within the electronic device can be increased in size, the displaying unit can be readily increased in size, and high functionality can be readily achieved by increasing the number of electronic components. Furthermore, since a portion with high flexibility can be reduced in size, for example, the risk of damage to a substrate caused by bending can be suppressed. Moreover, by opening and closing the first belt and the second belt on the basis of the hinge, a user can readily wear the electronic device.

Furthermore, for example, when the electronic device worn around the subject is viewed from the side, the electronic device may have a substantially elliptical shape.

Accordingly, by forming the electronic device into a semielliptical shape, which is similar to the cross-sectional shape of the wrist, fittability of the electronic device on the arm is improved.

Furthermore, for example, the first belt may have a substantially semielliptical arc shape when viewed from the side of the electronic device, and the second belt may have a substantially semielliptical arc shape when viewed from the side.

Accordingly, the user can readily wear the electronic device. In other words, an electronic device with improved fittability is achieved.

Furthermore, for example, an inner surface of the second end of the first belt may be provided with a first engagement unit, and the outer surface of the second belt may be provided with a second engagement unit. When the electronic device is worn around the subject, the first engagement unit and the second engagement unit may engage with each other.

Furthermore, for example, when the electronic device worn around the subject is viewed from the side and is divided into a first portion, which includes a boundary between the hinge and the first belt, and a second portion, which includes a boundary between the hinge and the second belt, by a line, which extends through the center of the substantially elliptical shape and the middle of the hinge in the circumferential direction, the second engagement unit may be provided at the outer surface of the second belt included in the second portion.

Accordingly, the second engagement unit is provided at a position that allows the second end (i.e., the first engagement unit) of the first belt to bite into the second belt, so that a simple and efficient engagement mechanism is achieved.

CONCLUSION

An wearable electronic device according to one or a plurality of aspects has been described above based on the embodiments. The electronic device according to each of the above embodiments can enhance reliability while ensuring a non-flexible portion, and can also be readily worn around a user.

The present disclosure is not limited to these embodiments or modifications thereof. The present disclosure includes an embodiment achieved by implementing various modifications conceivable by a skilled person to each of the above embodiments or modifications thereof, or an embodiment achieved by combining components in different embodiments or modification thereof within a scope that does not depart from the spirit of the present disclosure.

For example, although the electronic device according to each of the above embodiments is described as being of an arm-wearable type, the electronic device may be of a type worn on other parts of the body.

The electronic device according to the present disclosure is suitable as a highly-reliable, readily-wearable electronic device.

What is claimed is:
1. A wearable electronic device, comprising:
a first belt, front surface of the first belt being provided with a display having a curved display face;
a second belt;
a hinge that connects a first end of the first belt to a first end of the second belt, a shape formed by the first belt and the second belt capable of being an elliptical shape when the wearable electronic device worn around a subject is viewed from a side of the wearable electric device, and the hinge having higher flexibility than the first belt and the second belt;
a first engagement unit that is provided at a second end and a rear surface of the first belt, the second end of the first belt being opposite the first end of the first belt, and the first engagement unit being provided in a region of the rear surface of the first belt, in the region, the elliptical shape having smaller curvature than other regions of the elliptical shape; and
a second engagement unit that is provided at an outer side of the second belt and that engages with the first engagement unit.
2. The wearable electronic device according to claim 1, wherein the first belt is capable of being semielliptical arc shape when the wearable electronic device is viewed from a side of the wearable electronic device, and
wherein the second belt is capable of being semielliptical arc shape when the wearable electronic device is viewed from a side of the wearable electronic device.
3. The wearable electronic device according to claim 1, wherein when the wearable electronic device worn around the subject is viewed from the side of the wearable electronic device, the wearable electronic device is divided into a first portion and a second portion by a virtual line extending through a center of the elliptical shape and a middle of the hinge, and the second engagement unit is provided at an outer surface of the second belt within the second portion, the first portion extending from the middle of the hinge to a position where the virtual line intersects with the first belt, the second portion extending from the middle of the hinge to a position where the virtual line intersects with the second belt.
4. The wearable electronic device according to claim 1, wherein one of the first engagement unit and the second engagement unit has guide grooves, the guide grooves being arranged in a circumferential direction of the elliptical shape, and
wherein the other one of the first engagement unit and the second engagement unit has projections, the projections being fitted into the guide grooves when the wearable electronic device is worn around the subject.
5. The wearable electronic device according to claim 1, further comprising;
a third belt having higher flexibility than the first belt and the second belt, the third belt being connected to an edge side of the second engagement unit at a second end of the second belt, the second end of the second belt being opposite the first end of the second belt connected to the hinge, wherein when the electronic device is worn around the subject, the first belt overlaps an outer surface of the third belt.

6. The wearable electronic device according to claim 5, wherein the third belt includes a flexible battery therein.

7. The wearable electronic device according to claim 5, wherein the third belt includes a flexible battery, and a cover attached to one of principal surfaces of the flexible battery, wherein the cover has sidewalls along a side surface of the flexible battery, the side walls extending in a circumferential direction of the elliptical shape, and wherein the sidewalls include a plurality of protrusions that are arranged in the circumferential direction of the elliptical shape, gaps being interposed between each of the plurality of protrusions, and the plurality of protrusions protruding toward another one of the principal surfaces of the flexible battery.

8. The wearable electronic device according to claim 7, wherein when the third belt is bent toward the other one of the surfaces of the flexible battery, each of the protrusions contacts with the adjacent one or more of the protrusions.

9. The wearable electronic device according to claim 8, wherein when the cover is viewed from the other one of the surfaces of the flexible battery, each of the gaps is V-shaped, and wherein when the third belt is bent toward the other one of the surfaces of the flexible battery, each of the protrusions meshes with the adjacent one or more of the protrusions.

10. The wearable electronic device according to claim 7, wherein a bending regulation member is provided in each of the gaps, and wherein when the third belt is bent toward the other one of the surfaces of the flexible battery, each bending regulation member contacts with the protrusions adjacent to the bending regulation member.

11. The wearable electronic device according to claim 1, further comprising:

a sensor that is provided at the rear surface of the first belt and that contacts with the subject when the wearable electronic device is worn around the subject.

12. The wearable electronic device according to claim 1, further comprising:

a communication unit that is provided in the second belt and that communicates wirelessly with an external device.

13. The wearable electronic device according to claim 1, wherein the second belt is provided with a substrate equipped with a circuit, and wherein the hinge is provided with a flexible substrate that connects the display to the substrate.

14. The wearable electronic device according to claim 1, further comprising;

a battery, the first belt has the battery at a position other than a position where the displaying unit is provided in the first belt.

* * * * *